(«12») United States Patent
Sadoun

(10) Patent No.: US 11,622,918 B2
(45) Date of Patent: Apr. 11, 2023

(54) PREFORM FOR THE PRODUCTION OF A DENTAL PROSTHESIS

(71) Applicant: VITA ZAHNFABRIK H. RAUTER GmbH & CO KG, Bad Säckingen (DE)

(72) Inventor: Michael Sadoun, Esneux (BE)

(73) Assignee: VITA ZAHNFABRIK H. RAUTER GMBH & CO KG, Bad Säckingen (DE)

( * ) Notice: Subject to any disclaimer, the term of this patent is extended or adjusted under 35 U.S.C. 154(b) by 659 days.

(21) Appl. No.: 16/081,560

(22) PCT Filed: Apr. 28, 2017

(86) PCT No.: PCT/FR2017/051027
§ 371 (c)(1),
(2) Date: Aug. 31, 2018

(87) PCT Pub. No.: WO2017/149262
PCT Pub. Date: Sep. 8, 2017

(65) Prior Publication Data
US 2019/0091110 A1    Mar. 28, 2019

(30) Foreign Application Priority Data
Mar. 4, 2016   (FR) ...................................... 1651840

(51) Int. Cl.
*A61C 13/00*   (2006.01)
*A61K 6/802*   (2020.01)
(Continued)

(52) U.S. Cl.
CPC ................ *A61K 6/802* (2020.01); *A61C 5/70* (2017.02); *A61C 13/0022* (2013.01);
(Continued)

(58) Field of Classification Search
CPC .. A61K 6/802; A61K 6/17; A61C 5/70; A61C 13/0022; A61C 13/04;
(Continued)

(56) References Cited

U.S. PATENT DOCUMENTS 5,250,352 A     10/1993  Tyszblat
5,843,348 A *  12/1998  Giordano ............... A61K 6/802
                                                              264/19

(Continued)

FOREIGN PATENT DOCUMENTS

EP          0240643 A1     10/1987
EP          0241384 A2     10/1987
(Continued)

OTHER PUBLICATIONS

Corresponding International Application, Application No. PCT/FR2017/051027, International Search Report, dated Aug. 9, 2017, 6 pages.

(Continued)

*Primary Examiner* — Yogesh P Patel
(74) *Attorney, Agent, or Firm* — Ronald M. Kachmarik; Cooper Legal Group LLC

(57) ABSTRACT

A preform intended for the production of a dental prosthesis. The preform includes a group of agglomerated ceramic, glass-ceramic or glass particles, such that, as volume percents: more than 40% and less than 90% of the particles of said group have a size greater than 0.5 μm and less than 3.5 μm, said particles hereinafter being denoted "enamel particles", and more than 10% and less than 60% of the particles of said group have a size greater than 3.5 μm and less than 5.5 μm, said particles hereinafter being denoted "dentine particles." The microstructure of the preform is such that there is an axis X, termed "axis of variation", along which the Ve/(Ve+Vd) ratio changes continuously, Ve and Vd (Continued)

denoting the volume percents of enamel particles and of dentine particles, respectively. The enamel and dentine particles representing, together, more than 90% of the volume of the agglomerated particles.

11 Claims, 3 Drawing Sheets

(51) Int. Cl.

| | | |
|---|---|---|
| *A61C 13/083* | (2006.01) | |
| *C04B 41/83* | (2006.01) | |
| *C04B 35/111* | (2006.01) | |
| *C04B 41/00* | (2006.01) | |
| *C04B 38/00* | (2006.01) | |
| *C04B 35/64* | (2006.01) | |
| *C04B 41/48* | (2006.01) | |
| *A61K 6/17* | (2020.01) | |
| *A61C 5/70* | (2017.01) | |
| *A61C 13/34* | (2006.01) | |
| *A61C 13/01* | (2006.01) | |
| *C04B 111/00* | (2006.01) | |

(52) U.S. Cl.
CPC ............ *A61C 13/04* (2013.01); *A61C 13/083* (2013.01); *A61C 13/34* (2013.01); *A61K 6/17* (2020.01); *C04B 35/111* (2013.01); *C04B 35/64* (2013.01); *C04B 38/0074* (2013.01); *C04B 41/009* (2013.01); *C04B 41/483* (2013.01); *C04B 41/4826* (2013.01); *C04B 41/83* (2013.01); *C04B 2111/00405* (2013.01); *C04B 2111/00612* (2013.01); *C04B 2111/00836* (2013.01); *C04B 2235/5445* (2013.01); *C04B 2235/5472* (2013.01); *C04B 2235/602* (2013.01); *C04B 2235/612* (2013.01); *C04B 2235/66* (2013.01); *C04B 2235/665* (2013.01); *C04B 2235/75* (2013.01); *C04B 2235/77* (2013.01); *C04B 2235/783* (2013.01); *C04B 2235/96* (2013.01); *C04B 2237/58* (2013.01); *Y10T 428/12229* (2015.01)

(58) Field of Classification Search
CPC ..... A61C 13/083; A61C 13/34; C04B 35/111; C04B 35/64; C04B 38/0074; C04B 41/009; C04B 41/4826; C04B 41/483; C04B 41/83; C04B 2111/00405; C04B 2111/00612; C04B 2111/00836; C04B 2235/5445; C04B 2235/5472; C04B 2235/602; C04B 2235/612; C04B 2235/66; C04B 2235/665; C04B 2235/75; C04B 2235/77; C04B 2235/783; C04B 2235/96; C04B 2237/58; Y10T 428/12229

See application file for complete search history.

(56) References Cited

U.S. PATENT DOCUMENTS

| | | | |
|---|---|---|---|
| 5,869,548 A | 2/1999 | Ikushima et al. | |
| 6,673,300 B2* | 1/2004 | Allen | B01D 46/0001 |
| | | | 264/156 |
| 7,294,392 B2 | 11/2007 | Aechtner | |
| 7,845,947 B2* | 12/2010 | Rusin | A61C 13/0022 |
| | | | 433/223 |
| 2005/0008887 A1* | 1/2005 | Haymann | A61C 5/77 |
| | | | 428/542.8 |
| 2010/0292522 A1* | 11/2010 | Chun | C04B 35/488 |
| | | | 585/648 |
| 2014/0336304 A1* | 11/2014 | Ruppert | A61K 6/30 |
| | | | 523/116 |
| 2016/0095798 A1* | 4/2016 | Brodkin | A61C 7/08 |
| | | | 428/402 |
| 2020/0392005 A1* | 12/2020 | Yu | B01J 13/04 |

FOREIGN PATENT DOCUMENTS

| | | |
|---|---|---|
| EP | 0701808 A2 | 3/1996 |
| EP | 2725358 A1 | 4/2014 |
| FR | 2904306 A1 | 2/2008 |
| FR | 2935897 A1 | 3/2010 |
| WO | 199307846 | 4/1993 |
| WO | 2010029515 A1 | 3/2010 |
| WO | 2015168463 A1 | 11/2015 |

OTHER PUBLICATIONS

Chun Hong Chen et al: "Fabrication and Characterization of Porous Alumina Tube with Pore Gradient" Materials Science Forum, vol. 492-493. Aug. 15, 2005 (Aug. 15, 2005), pp. 755-760, XP055316988, DOI:10.4028/www.scientific.net/MSF.492-493.755, cited in the application, "Introduction Experimental Procedure"; 22-24 figures 1-9.
Figiel Pawel et al: "Al2O3 and ZrO2powders formed by centrifugal compaction using the ultra HCP method" Ceramics International. vol. 39. No. 1, 2013, pp. 635-640. XP028955615, ISSN: 0272-8842, DOI:10.1016/J.CERAMINT.2012.06.075, cited in the application 1. Introduction; 2. Experimental procedure; 4. Conclusions; figures 6-11.

* cited by examiner

PREFORM FOR THE PRODUCTION OF A DENTAL PROSTHESIS

TECHNICAL FIELD

The invention relates to a preform, to a porous support obtained by sintering such a preform, to a composite block obtained by impregnation of such a porous support by means of a resin, and to a dental prosthesis produced from such a composite block.

The invention also relates to a process for producing such a preform, such a porous support and such a composite block, and to a process for producing a dental prosthesis from such a composite block.

PRIOR ART

Composite blocks comprising a support, generally made of ceramic material, and a resin which at least partially fills the interstices of the support are known.

Conventionally, the porous support, before infiltration by the resin, is obtained by sintering a preform.

To produce the composite block, resin in the liquid state is infiltrated into the accessible, or "open", pores of the support, generally by capillary action. After curing of the resin, the composite block obtained is machined to the desired definitive shape, conventionally by "computer aided design—computer aided machining" or CAD-CAM.

Processes for producing composite blocks are in particular described in the following documents: U.S. Pat. Nos. 5,869,548, 5,843,348, 5,250,352, EP 0 241 384, WO 93/07846, EP 2 725 358, EP 0 240 643, FR 2 904 306, EP 0 701 808 or U.S. 7,294,392.

WO 2010/029515 also describes a composite block intended for the production of a dental prosthesis.

U.S. Ser. No. 13/063,365 describes a process for high-pressure infiltration of a porous support by means of a resin.

Moreover, the Search Report of French application 16 51840 cites several documents:

The article "*Fabrication and Characterization of Porous Alumina Tube with Pore Gradient*" by C. H. Chen et al., in "*Materials Science Forum*" 492-493, pp. 755-760, describes the production of porous tubes by centrifugation of a powder of which the unimodal solid fraction has a mean particle size of 0.5 µm, and particles of a pore-forming agent. The objective of the centrifugation is to modify the porosity, and not the distribution of the grain size.

U.S. Pat. No. 5,843,348 describes a process in which a suspension may be formed by centrifugation. This centrifugation is an alternative to pressure forming. The centrifugation is thus used as a means of compaction, and not as a means for creating a gradient of properties of the structure. In addition, this document does not suggest a bimodal particle size distribution for the suspension in order to obtain a gradient in the particle sizes.

The article entitled "*Al$_2$O$_3$ and ZrO$_2$ powders formed by centrifugal compaction using the ultra HCP method*", by P. Figiel et al., in "*Ceramics international*" 39 (2013) 635-640, focusses on the influence of the compaction by centrifugation on sintered products obtained by centrifugation of suspensions of Al$_2$O$_3$ and ZrO$_2$ microparticles. The mixtures of Al$_2$O$_3$ and ZrO$_2$ particles result in black, opaque sintered products which are not suitable for the production of dental prostheses. In addition, D3 seeks to obtain a homogeneous sintered product, and therefore to avoid any gradient in the mechanical and optical properties.

The composite blocks produced according to current processes do not make it possible to produce dental prostheses which have optical and mechanical properties corresponding precisely to those of a natural tooth, which limits the commercial exploitation of these composite blocks.

There is therefore a need for composite blocks which make it possible to produce prostheses having optical and mechanical properties corresponding precisely to those of a natural tooth.

There is also a constant need to extend the lifetime of the prostheses obtained form composite blocks.

An aim of the invention is to at partially meet these needs.

SUMMARY OF THE INVENTION

According to the invention, this aim is achieved by means of a preform comprising, preferably consisting of, a group of agglomerated particles, preferably ceramic, glass-ceramic or glass particles, such that, as volume percents:

more than 40%, preferably more than 50%, preferably more than 60%, and less than 90% of the particles of said group have a size greater than 0.5 µm, preferably greater than 1.0 µm, preferably greater than 1.5 µm, preferably greater than 2.0 µm, and less than 3.5 µm, preferably less than 3.0 µm, said particles hereinafter being denoted "enamel particles", and more than 10%, preferably more than 20%, preferably more than 30%, and less than 60% of the particles of said group have a size greater than 3.5 µm, preferably greater than 4.0 µm, and less than 5.5 µm, preferably less than 5.0 µm, said particles hereinafter being denoted "dentine particles", the Ve/(Ve+Vd) ratio or "local density" continuously changing along an X axis, termed "axis of variation", Ve and Vd denoting the volume percents of enamel particles and of dentine particles, respectively.

As will be seen in greater detail in the remainder of the description, the continuous variation of the Ve/(Ve+Vd) ratio eliminates any trace of stratum, which makes it possible to produce a porous support having gradual variations in shades and/or in mechanical properties. Advantageously, the dental prosthesis obtained from such a support comes without any interface line between various regions of the prosthesis.

The variation in the Ve/(Ve+Vd) ratio expresses the presence of a gradient in the particle sizes. Such a gradient does not correspond to a gradient in the pore size, nor in the amount of pores.

In particular, when the preform is produced by centrifugation of a suspension comprising particles and a solvent, as described hereinafter, the porosity characteristics depend on many parameters, such as the shape of the particles, the particle size distribution of the particles, the density of the constituent material of the particles, the surface properties of the particles, and in particular the zeta potential, the pH of the solvent, the strength of the centrifugation, the centrifugation time, etc. Characteristics relating to the particle size distribution could not therefore be deduced from characteristics relating to the pore size distribution or relating to the amount of pores.

A preform according to the invention may also comprise one or more of the following optional characteristics:

the enamel particles have a mean size D$_{50}$ greater than 1.5 µm and less than 3.0 µm, and/or the dentine particles have a mean size D$_{50}$ greater than 4.0 µm and less than 5.0 µm;

along the axis of variation, the volume percent of enamel particles in the opposite way, preferably in the complementary way, to the volume percent of dentine particles;

along the axis of variation, the concentration of enamel particles and of dentine particles, that is to say the total volume of enamel particles and dentine particles per unit of volume of the preform, exhibits a variation of less than 20%, preferably less than 10%, relative to its minimum value along said axis of variation, the unit of volume being a volume of 1 mm³;

the preform has a first region, termed "enamel region", in which the Ve/(Ve+Vd) ratio is greater than 0.6, preferably greater than 0.7, preferably greater than 0.8, preferably greater than 0.9, and a second region, termed "dentine region", in which the Ve/(Ve+Vd) ratio is less than 0.5, preferably less than 0.4, preferably less than 0.3, preferably less than 0.2, preferably less than 0.05, the enamel and dentine regions preferably being in the form of layers and preferably extending from opposite enamel and dentine faces of the preform, taking into consideration the axis of variation;

the enamel and dentine particles together represent more than 60%, preferably more than 70%, preferably more than 80%, preferably more than 90%, preferably more than 95%, preferably more than 98%, preferably substantially 100% of the volume of the mass of said group of particles;

more than 90%, preferably more than 95%, preferably more than 98% of the group consisting of the enamel particles and the dentine particles, as number percent, are made of a material which has a refractive index of greater than 1.40, preferably greater than 1.45 and/or less than 1.70, preferably less than 1.65;

preferably, the density $\rho_e$ of the enamel particles is substantially identical density $\rho_d$ of the dentine particles;

preferably, the $p_e/p_d$ ratio is greater than 0.9, preferably greater than 0.95, preferably greater than 0.98 and less than 1.10, preferably less than 1.05, preferably less than 1.02;

preferably, the group consisting of the enamel particles and the dentine particles comprises less than 1%, preferably less than 0.5%, preferably less than 0.1%, as weight percent, of zirconium oxide, preferably comprises no zirconium oxide.

The invention also relates to a process for producing a preform according to the invention, said process comprising the following steps:

A) preparing a suspension comprising, preferably consisting of:
  a group of particles, or "particulate feedstock", preferably of ceramic, glass-ceramic or glass particles, said group comprising, as volume percents on the basis of the volume of the mass of said group of particles:
    more than 30%, preferably more than 40%, and less than 70% of enamel particles,
    more than 30%, preferably more than 40%, and less than 70% of dentine particles,
  a solvent;

B) modifying the spatial distribution of the particles of the suspension, preferably by centrifugation of the suspension;

C) consolidating the particles so as to form a preform.

As will be seen in greater detail in the remainder of the description, modifying the spatial distribution of the particles of the suspension, made, possible by the use of a specific bimodal solid fraction, makes it possible to locally adjust the Ve/(Ve+Vd) ratio, and thus to adjust the appearance, but also the local mechanical properties, of the preform and consequently of the sintered porous support, of the composite block and of the prosthesis.

The invention also relates to a process for producing a porous support, said process comprising a production of a preform according to the invention, then a step D) of sintering said preform, the intensity of the sintering being variable as a function of the region of the preform under consideration.

Such a process may also comprise one or more of the following optional characteristics:

the intensity of the sintering of a region of the preform is variable as a function of its position in the preform, preferably as a function of its position along the axis of variation;

step D) comprises
  a basic sintering, preferably carried out for a period of greater than 1 h and less than 4 h, during which the entire external surface of the preform receives substantially the same density of heat flow (homogeneous sintering); and
  an additional sintering, preferably carried out at a temperature more than 30° C., more than 50° C., or even more than 100° C., more than 150° C. or more than 200° C. above the temperature of the basic sintering, for a period of preferably greater than 15 min and preferably less than 4 h, during which the density of heat flow is variable as a function of the part of the external surface of the preform under consideration, during the additional sintering, the higher the Ve/(Ve+Vd) ratio, the higher the density of heat flow, that is to say the intensity of the sintering;

during the additional sintering, one face of the preform in proximity to which the concentration of enamel particles is the highest, termed "enamel face", sits on a hot plate.

The invention also relates to a porous support produced according to a process according to the invention, said support comprising a region which has an open porosity of between 5% and 20%, termed "porous region", and a region which has an open porosity of greater than 20% and less than 40%, termed "very porous region", said porous and very porous regions each having a volume of greater than 30 mm³, preferably greater than 50 mm³, preferably greater than 1.00 mm³, preferably greater than 150 mm³.

Preferably, if the thickness along the axis of variation X is measured, said porous and very porous regions are in the form of layers with a thickness of greater than 1 mm, preferably greater than 3 mm, preferably greater than 5 min.

The invention also relates to a process for producing a composite block, said process comprising a production of a porous support according to a process according to the invention, then steps E) and F) as follows:

E) infiltrating the porous support by means of a resin in the liquid state;

F) curing all the resin in the liquid state impregnating the support;

steps E) and F) being carried out under a pressure of preferably greater than 1000 bar.

Finally, the invention relates to a composite block, in particular produced according to a production process according to the invention, the composite block comprising a "very hard" region having a hardness of greater than 240 Vickers, and preferably a Young's elastic modulus, measured according to ISO standard 10 477, of greater than 30 GPa, and a "hard" region having a hardness of greater than 60 Vickers and less than 180 Vickers, preferably less than 170 Vickers, or even less than 160 Vickers, and preferably a Young's elastic modulus, measured according to ISO standard 10 477, of greater than 15 GPa and less than 30 GPa.

Said very hard and hard regions preferably correspond to porous and very porous regions, respectively, of the porous support of origin. Preferably, they each have a volume of greater than 30 mm$^3$, preferably greater than 50 mm$^3$, preferably greater than 100 mm$^3$, preferably greater than 150 mm$^3$.

More preferably, if the thickness along the axis of variation X is measured, said very hard and hard regions are in the form of layers with a thickness of greater than 1 mm, preferably greater than 3 mm, preferably greater than 5 mm.

BRIEF DESCRIPTION OF THE FIGURES

Other characteristics and advantages of the invention will further emerge on reading the detailed description which follows and on examination of the appended drawing, provided for illustrative and non-limiting purposes, in which.

DEFINITIONS

Figure 1:
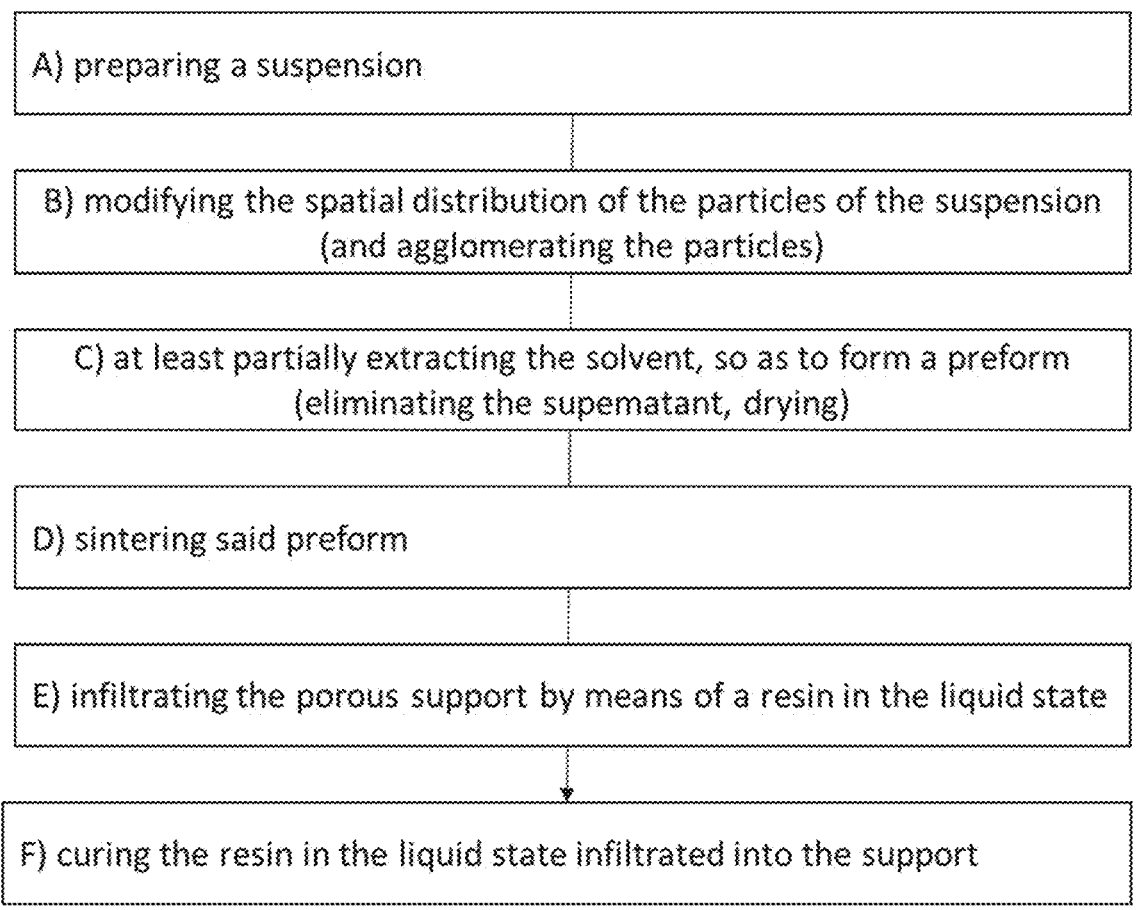
FIG. 1 shows a process for producing a dental prosthesis according to the invention.

A "preform" is conventionally a solid mass with open porosity consisting of agglomerated particles, i.e. particles fastened together without sintering or melting of these particles. This agglomeration may result in particular from compaction of the particles, preferably without plastic deformation of the particles, or from mixing of the particles with a binder or without binder.

The term "dental prosthesis" is generally intended to mean any part intended to be placed on the teeth of a patient for the purpose of totally or partly restoring them to their natural form and their natural function.

Thus, the dental prostheses manufactured according to the invention may be, for example, peripheral or crown caps which are placed on the stump of a natural tooth, or else prostheses generally denoted under the terms "inlay" and "onlay" which are intended to reconstitute a partial modification of a tooth by filling the cavity resulting from the loss of substance of the tooth with a part of the same shape made by the dental technician, or else bridges which are prostheses which simultaneously rest on the remaining parts of at least two teeth while optionally compensating for one or more of the missing teeth, or else dental crowns screwed onto implants.

Depending on the nature of the dental prosthesis manufactured, a composite block according to the invention may be rigidly connected to other parts, for example a metal base.

The "size" of a particle of a powder is conventionally given by a particle size distribution characterization. A laser particle size analyzer makes it possible to measure sizes of less than or equal to 5 mm.

The percentiles or "centiles" 10 ($D_{10}$), 50 ($D_{50}$), 90 ($D_{90}$) and 99.5 ($D_{99.5}$) of a powder are the sizes of particles corresponding to percentages, by weight, of 10%, 50%, 90% and 99.5% respectively, on the cumulative particle size distribution curve of the particles of the powder, the particle sizes being classified in increasing order. For example, 10% by weight of the particles of the powder have a size less than $D_{10}$ and 90% of the particles, by weight, have a size greater than $D_{10}$. The percentiles may be determined by means of a particle size distribution produced using a laser particle size analyzer.

The term "maximum size" refers to the 99.5 percentile ($D_{99.5}$) of said powder.

The term "median size" refers to the $D_{50}$ percentile, i.e. the size dividing the particles into first and second populations equal by weight, these first and second populations comprising only particles having a size greater than, or less than, respectively, the median size.

In a preform, the particles are no longer in the form of a powder, but are agglomerated by compaction or by means of a binder, preferably a temporary binder. Their sizes are, however, the same as those that they had in the starting filler that was prepared to form the preform. The size of the particles within the preform may therefore be evaluated on the basis of the characteristics of the powders used to constitute the starting filler. The size of the particles in the preform may also be conventionally evaluated by means of image analyses of preform sections. These images may in particular be obtained by Scanning Electron Microscopy (SEM).

The sintering of the preform results in a porous support. During the sintering, sintering necks form and the particles attach solidly to one another. Their sizes are not however substantially modified. Image analyses of sections of the support thus also make it possible to evaluate the particle size distribution of the particles of the preform.

The mean pore size may be conventionally measured with a mercury porosimeter.

Unless otherwise indicated, "containing a", "comprising a" or "having a" should be interpreted non-exclusively.

The volume percents relating to particles, for example the percentages of enamel particles Ve and of dentine particles Vd, are percentages on the basis of the mass of these particles, i.e. ignoring the interstices between the particles.

1 bar is equal to 0.1 MPa.

DETAILED DESCRIPTION

Preform

Figure 3:
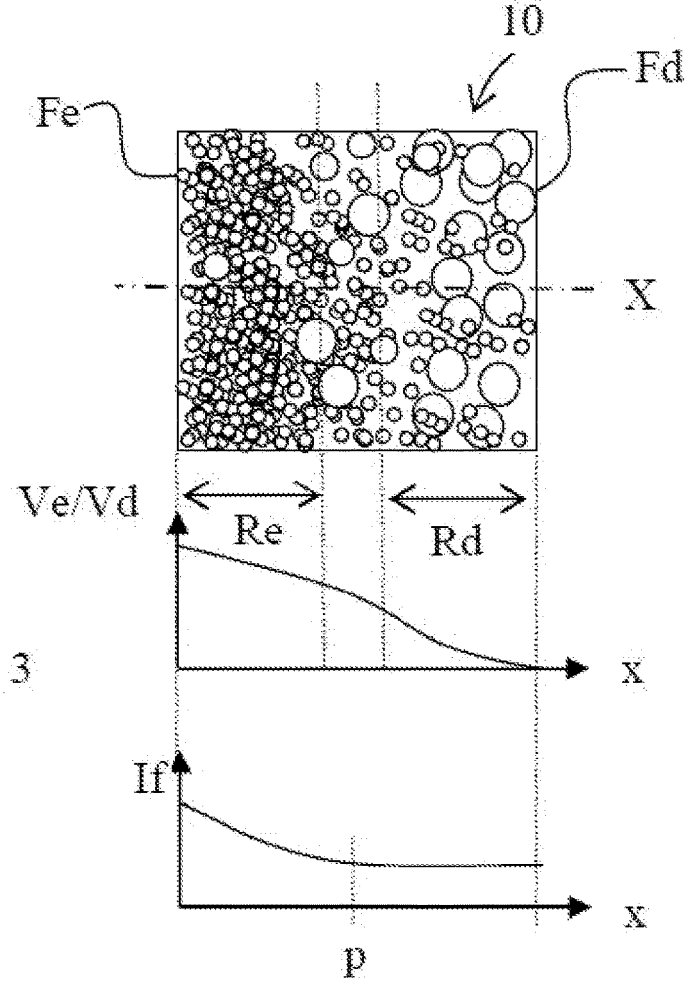

As represented in FIG. 3, a preform 10 according to the invention consists of a group of agglomerated particles.

The constituent material of the particles may be any material commonly used for the production of dental prostheses.

Preferably, more than 50%, more than 70%, more than 90%, preferably more than 95%, preferably more than 98%, preferably 100% by volume of the particles of said group are one and the same material, preferably ceramic.

Preferably, the material is made of one or more metal oxides, in the form of glass-ceramic, glass or crystalline ceramic such as quartz, alumina or mullite.

Preferably, the maximum size of the group of particles is greater than 1 μm and/or less than 10 μm.

Preferably, the minimum size of the group of particles is greater than 0.01 μm and/or less than 0.5 μm.

Preferably, the median size of the group of particles is greater than 1 μm and/or less than 10 μm.

According to the invention, the spatial distribution of the particles depends on their sizes. In particular, there are regions in which the volume percents of the enamel particles Pe, that is to say of the very fine particles having a size greater than 1.5 μm and less than 3.5 μm, are different.

There are also regions in which the volume percents of the dentine particles Pd, that is to say of the fine particles having a size of greater than 3.5 μm and less than 5.5 μm, are different.

The volume percent may be evaluated by dividing the volume occupied by the particles under consideration by the volume of the region under consideration. The region may for example be a 1 mm-sided cubic region.

Preferably, along the axis of variation X, the volume percent of enamel particles varies inversely, preferably in an inversely proportional manner, to the volume percent of dentine particles, that is to say the fewer dentine particles a region comprises, the more enamel particles it comprises, as represented in FIG. 3.

Preferably, the enamel and dentine particles together represent more than 60%, more than 70%, or even more than 80% of the preform, as volume percent.

The particle size distribution (number of particles as a function of the size of the particles) of the group of particles is bimodal, that is to say comprises first and second principle modes, the first principle mode being greater than 1.5 μm, preferably greater than 2.0 μm, and less than 3.5 μm, preferably less than 3.0 μm, the second mode being greater than 3.5 μm, preferably greater than 4.0 μm, and less than 5.5 μm, preferably less than 5.0 μm. The Ve/(Ve+Vd) ratio changes continuously along an axis X, termed "axis of variation". The axis of variation may be rectilinear or non-rectilinear. It is preferably rectilinear.

A "continuous" change corresponds to a change such that, along the axis of variation, there is no stationary phase for the Ve/(Ve+Vd) ratio, except optionally in the extreme region parts of the preform.

Preferably, within the preform, there is no stationary phase for the Ve/(Ve+Vd) ratio, which thus changes constantly along the axis of variation.

Preferably, as represented in FIG. 3, within the preform, the change in the Ve/(Ve+Vd) ratio is monotonic, that is to say that this ratio is always increasing or decreasing, along the axis of heterogeneity.

Preferably, within the preform, the preform has a first region, term "enamel region", in which the Ve/(Ve+Vd) ratio is greater than 0.9, and a second region, termed "dentine region", in which the Ve/(Ve+Vd) ratio is less than 0.05.

Preferably, within the preform, each of the enamel and dentine regions has a volume of greater than 30 mm³, preferably greater than 50 mm³, preferably greater than 100 mm³, preferably greater than 150 mm³.

Preferably, the Ve/(Ve+Vd) ratio changes identically along any line parallel to the axis of variation. Thus, in a slice of the preform perpendicular to the axis of variation, of very small thickness, the Ve/(Ve+Vd) ratio is substantially constant.

Preferably, the enamel and dentine regions are therefore in the form of layers, preferably extending from opposite faces of enamel Fe and of dentine Fd of the preform, preferably substantially perpendicularly to the axis of variation.

Preferably, each of said layers has a thickness of greater than 1 mm, preferably greater than 2 ram, preferably greater than 3 mm, preferably greater than 4 mm, preferably greater than 5 mm Preferably, there is at least one region of enamel and one region of dentine occupying, together, more than 70%, more than 80%, more than 90%, preferably 100% of the volume of the preform.

Process for Producing the Preform

A process comprising steps A) to C) is very suitable for producing a preform according to the invention.

In step A), a suspension is conventionally prepared by mixing powders in a solvent 4, in a container.

The solid fraction of the suspension preferably represents more than 50%, preferably more than 60%, by volume, and less than 75%, preferably less than 70%, by volume, of the suspension.

Preferably, a first powder of particles Pe having a median size of greater than 1.5 μm, preferably greater than 2.0 μm, and less than 3.5 μm, preferably less than 3.0 μm, or "enamel powder", and a second powder of particles Pd having a median size of greater than 3.5 μm, preferably greater than 4.0 μm, and less than 5.5 μm, preferably less than 5.0 μm, or "dentine powder" are mixed. Preferably, the first and second powders together represent more than 90%, more than 95%, preferably 100% of the mass of the solid fraction.

Preferably, the solid fraction consists of the enamel and dentine powders.

Preferably, the solid fraction does not comprise pore-forming agent. Advantageously, the mechanical properties are thereby improved.

Preferably, more than 90%, more than 95%, preferably 100% of the mass of the solid fraction consists of particles made of one or more metal oxides, in the form of glass-ceramic, glass, or crystalline ceramic such as quartz, alumina or mullite.

In one embodiment, the dentine particles contain colored pigments, in particular colored pigments conventionally used for the production of dental prostheses.

In one embodiment, the enamel particles do not contain colored pigments.

The only variation in the spatial distribution of the particles in fact makes it possible to obtain variations in shades corresponding to the natural variations of teeth.

The solvent is preferably chosen from the group consisting of water and water+ethanol mixtures. Conventionally, it may also contain a pH modifier, for example hydrochloric acid and/or acetic acid, and/or a deflocculant, for example sodium polymethacrylate and/or sodium silicate, and/or sodium polycarboxylate, and/or a binder, for example polyvinyl alcohol. Preferably, the solvent does not comprise pore-forming agent, such as PMMA.

In step B), the container is preferably rotated, preferably about an axis of rotation Y, so as to centrifuge the suspension and thus to create segregation between the particles.

Figure 2:
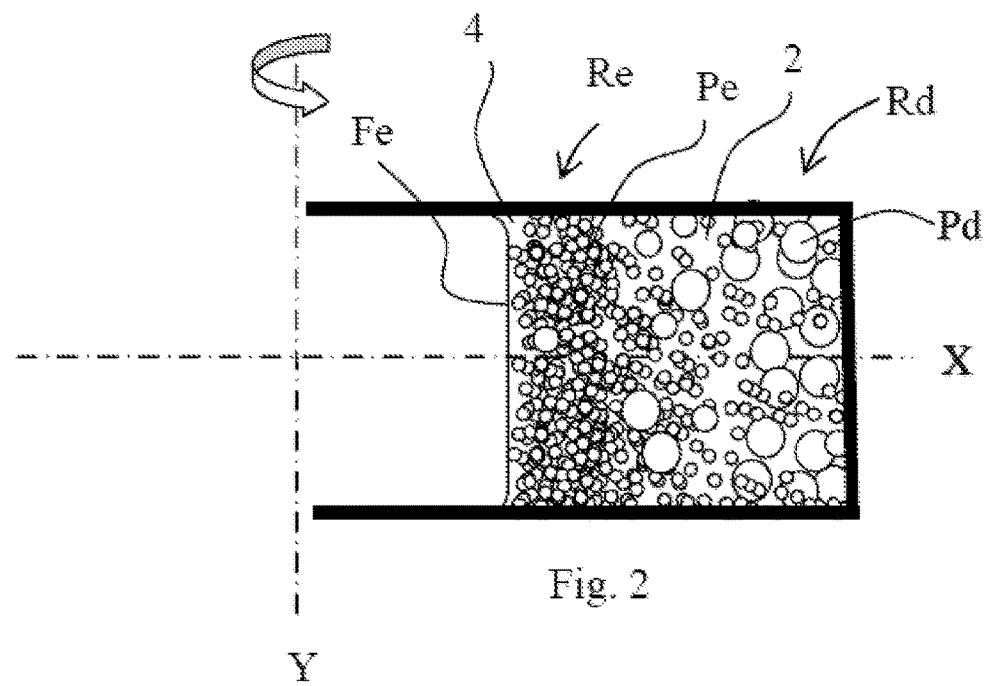
FIGS. 2 and 3, and 4, illustrate very diagrammatically steps B) and D), respectively, of a process for producing a dental prosthesis according to the invention.

During a centrifugation, as represented in FIG. 2, the spatial distribution of the particles of the suspension varies according to the direction of the centrifugal force. When all the particles are made of the same material and have similar shapes and densities, the concentration of coarse particles increases as the distance from the center of rotation increases, along the axis of variation X corresponding to the direction of the centrifugal force and therefore perpendicular to the axis of rotation Y.

The variation of the centrifugation conditions and of the viscosity of e suspension makes it possible to adjust the spatial distribution of the particles.

Centrifugation is a known process for producing homogeneous and compact preforms. Centrifugation is thus conventionally used with suspensions of which the solid fraction is unimodal, in order to prevent any heterogeneity.

The inventors have discovered that centrifugation, applied to a suspension comprising a specifical bimodal solid fraction, makes it possible to create heterogeneity in the particle size distribution, and to finally obtain a composite block having mechanical and appearance properties that are variable as a function of the region under consideration. As previously indicated, this heterogeneity in the particle sizes does not involve a change in the porosity, or even in the pore size.

The centrifugation conditions are the rotational speed and the centrifugation time.

In a well-known manner, for one and the same suspension, the segregation of the particles increases with the strength of the centrifugation, that is to say with the rotational speed and the centrifugation time. The effect of the centrifugation depends, in a known manner, on the nature of the solvent, and in particular on its viscosity, but also on the parameters of the particles, and in particular on their composition and their shape. Simple tests make it possible to determine suitable centrifugation conditions.

The face of the suspension which is closest to the axis of rotation Y during the centrifugation is called the "enamel face" Fe. When the particles of the suspension all have substantially the same density, it is in proximity to this face that the concentration of particles of smaller sizes is the highest. In particular, it is in proximity to this face that the concentration of enamel particles is the highest.

The centrifugation contributes to the agglomeration of the particles.

The centrifugation produces an acceleration preferably greater than 50 G, preferably greater than 80 G, preferably greater than 100 G, preferably greater than 130 G, or even greater than 150 G.

The centrifugation time is preferably greater than 10 min, preferably greater than 20 min, or even greater than 30 min.

In step C), the solvent is extracted from the suspension, thereby making it possible to reinforce the particle agglomeration.

Preferably, after the centrifugation, the supernatant is poured out of the suspension. It may also be eliminated by heating under vacuum.

Drying is then carried out in order to eliminate the liquid between the agglomerated particles.

At the end of step C), a preform according to the invention is obtained, as represented in FIG. 3.

Process for Producing a Porous Support from the Preform

The invention also relates to a process for producing a porous support, comprising steps A) to C) so as to produce a preform according to the invention, then a step D) of sintering said preform.

In one embodiment, the preform undergoes a basic sintering, which is preferably substantially homogeneous. The sintering temperature depends on the nature of the particles. Those skilled in the art know how to adjust this temperature according to the nature of the particles.

The duration of the basic sintering is preferably greater than 1 h, preferably greater than 2 h, preferably greater than 3 h, and/or less than 5 h, preferably less than 3 h, preferably less than 2.5 h, preferably less than 2.25 h.

The basic sintering is preferably substantially homogeneous, that is to say that the heat flow densities (in $W/m^2$) are substantially the same whatever the part of the external surface of the preform under consideration.

The temperature increase and decrease gradients may, for example, be between 25° C. and 300° C./hour.

The furnace 20 used for the basic sintering may be a conventional sintering furnace. In one particularly preferred embodiment, the sintering conditions are differential, that is to say that they depend on the region of the preform under consideration. Variation in the sintering conditions makes it possible to locally adjust the density of the support.

If there is no differential sintering, the porous support makes it possible to produce a composite block which has a gradient of optical properties, but is substantially without a gradient of mechanical properties, the enamel particles being the smallest. However, the mechanical properties of a natural tooth are different depending on the region under consideration. In particular the enamel and the dentine do not have the same mechanical properties.

The differential sintering advantageously makes it possible to adapt the mechanical properties of various regions of the composite block to the corresponding regions of the natural tooth. In particular, preferably, the sintering is reinforced in the enamel region in order to reduce the open porosity and to increase the local density. After impregnation with the resin, the enamel region of the composite block advantageously has a greater hardness, a higher elastic modulus and a higher wear resistance.

The sintering conditions are the sintering temperature and the sintering time, or "sintering stationary phase", that is to say the duration for which the sintering temperature is maintained. In a well-known manner, the density of a region of the support increases with the sintering intensity, that is to say with the sintering temperature and the sintering duration.

Figure 4:
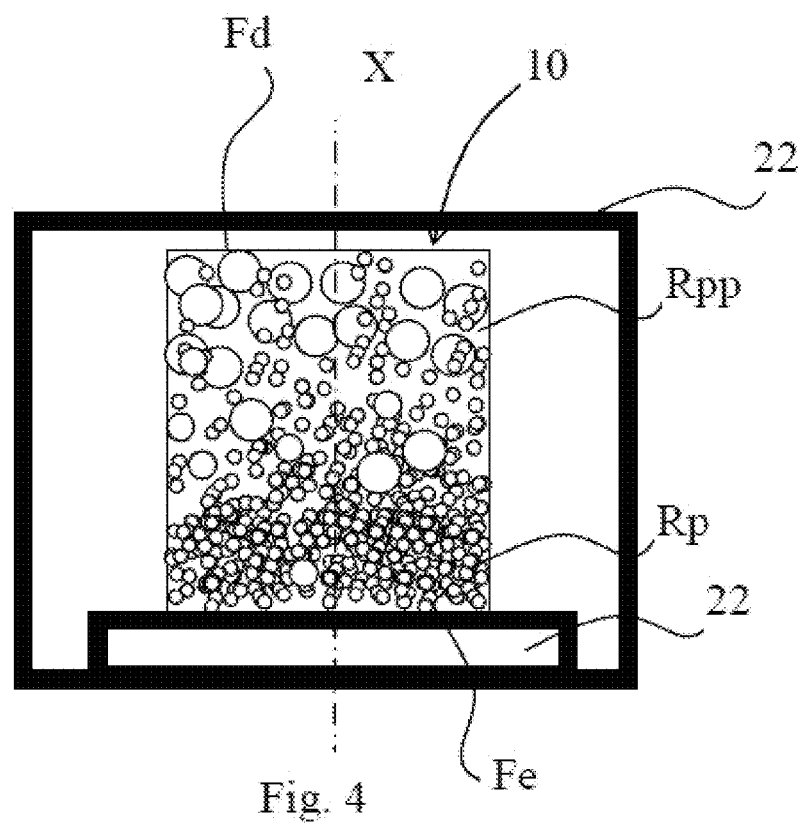

Preferably, the intensity of the sintering of a first region, termed "porous region", is greater than the intensity of the sintering of a second region, termed "very porous region", as represented in FIG. 4.

The porous region preferably comprises a Ve/(Ve+Vd) ratio that is higher than the Ve/(Ve+Vd) ratio of the very porous region.

Preferably, the porous region undergoes, in addition to the basic sintering, an additional sintering, that the very porous region does not undergo. The duration of the additional sintering is preferably greater than 15 min, preferably greater than 30 min, preferably greater than 1 h, and/or less than 2 h, preferably less than 3 h, preferably less than 2.5 h, preferably less than 2.25 h.

Preferably, for the additional sintering, the preform is heated in a preferred direction, termed "heating direction", that is to say that the heat emitted by the heat source penetrates into the preform in a preferred manner in the heating direction. Preferably, the preform is placed opposite a heat source, which is preferably placed, via a lower face, preferably the enamel face Fe, on a hot plate 22, for example placed in the furnace 20. The sintering intensity thus decreases as the distance from the heat source increases, up to the opposite face or "dentine face" Fd.

When the preform is heated along a heating direction, varying the duration of the additional sintering advantageously makes it possible to modify the depth of the region of the preform which is affected by the additional sintering, but also the intensity of the sintering as a function of the depth.

More preferably, the additional sintering is carried out immediately after the basic sintering, without the preform being moved in the furnace between the two sinterings. Preferably, the preform is initially placed, by its enamel face, on the hot plate 22 placed in the furnace 20. For the basic sintering, the inside of the furnace is heated, the hot plate being turned off. The heating is then substantially homogeneous. The hot plate is then turned on in order to provide additional sintering of the enamel region.

The additional sintering may be carried out without turning off the furnace or after having turned off the furnace.

The additional sintering may be carried out while the basic sintering is continuing or after said basic sintering has been completed, for a part of the preform.

Preferably, the additional sintering is carried out while the basic sintering continues for a part of the preform.

In the case of the use of a hot plate, as described above, the enamel face is preferably heated by the hot plate, while the other faces remain at the sintering temperature of the basic sintering. After the hot plate has been turned on, the homogeneous sintering therefore then continues only for a part of the preform.

The additional sintering therefore locally reinforces the basic sintering. Preferably, the additional sintering is then reflected by a local increase in the temperature greater than 30° C., preferably greater than 50° C., or even greater than 100° C., greater than 150° C. or greater than 200° C., preferably for a period greater than 10 min, preferably greater than 15 min, greater than 30 min, greater than 60 min.

As represented in FIG. 4, the heating direction is preferably substantially parallel to the axis of variation X of the preform, preferably in such a way that the region comprising, on average, the finest particles is the most heated. Preferably, this region corresponds to an enamel region of the preform.

The second curve of FIG. 3 represents the variation in sintering intensity If resulting from the additional sintering, as a function of the depth x, from the enamel face Fe of the preform placed on the hot plate 22, along the heating direction. Preferably, the sintering intensity decreases as far as a depth p, then remains substantially constant.

After the additional sintering, the porous region Rp thus has a density and a hardness which are greater than those of the very porous region Rpp (FIG. 4).

Preferably, the porous region has an open porosity which is less than 1%, preferably less than 5%, preferably less than 10% of the very porous region.

Preferably, any region of the support has an open porosity of greater than 10%, measured according to ISO standard 5017, thereby facilitating the infiltration of the resin.

More preferably, any region of the support has an open porosity of between 25% and 50%. The largest open-pore diameter is preferably between 0.1 μm and 1 μm.

Porous Support

The invention also relates to a porous support obtained by sintering a preform according to the invention.

The mean pore size in the porous region is preferably greater than 0.1 μm and less 0.3 μm.

The mean pore size in the very porous region is preferably greater than the mean pore size in the porous region. It is preferably greater than 0.2 μm and less than 0.3 μm.

The porous and very porous regions are preferably at two opposite ends of the support.

The porous region may be included in an enamel region or vice versa. Preferably, the porous region is substantially amalgamated with an enamel region.

The very porous region may be included in a dentine region or vice versa. Preferably, the very porous region is substantially amalgamated with a dentine region.

The correspondence between the porous region and the enamel region is in particular possible when the preform is placed on a hotplate by a face corresponding to the interior face of the suspension during centrifugation thereof, i.e. to the face closest to the center of rotation during the centrifugation.

The correspondence between the very porous region and the dentine region is also possible when the preform is placed on a hotplate via a face Fe corresponding to the interior face of the suspension during centrifugation thereof, i.e. to the face closest to the center of rotation during the centrifugation.

The invention is not limited by the chemical nature or the general shape of the support, provided that the support is sufficiently porous and comprises interconnected open pores, including in its mass.

Likewise preferably, before any infiltration of resin, the porous support, has on average, a density greater than 60% and/or less than 85%.

In one embodiment, the preform and/or the support have the general shape of a tooth or of a parallelepipedal block of dimensions substantially equivalent to those of a tooth, for example the largest dimension of which is less than 2 cm, preferably less than 11.5 cm and/or the smallest dimension of which is greater than 5 mm.

The preform and/or the support may also be in the shape of a disk, for example: of 100 mm diameter, preferably having a thickness greater than 10 mm and/or less than 25 mm, for example of 12 mm, 14 mm or 20 mm. The preform and/or the support must then be cut up to form blocks of dimensions substantially equal to those of a tooth.

The porous support is preferably made of a sintered ceramic material, preferably chosen from one or more metal oxides, in the form of glass-ceramic, glass, or crystalline ceramic such as quartz, alumina or mane.

Process for Producing a Composite Block from a Porous Support

The invention also relates to a process for producing a composite block, comprising steps A) to D) so as to produce a porous support according to the invention, then steps E) and F) below:

E) infiltrating the porous support by means of a resin in the liquid state;

F) curing the resin in the liquid state impregnating the support.

The composite block results from the curing of the infiltrated resin.

The known infiltration techniques may be used.

The resin may be a monomer or a mixture of monomers. Preferably, the resin in the liquid state comprises only a mixture of monomers and a catalyst.

Preferably, the composite block consists of the support impregnated with the cured resin, a single resin having been infiltrated into the support. Varying the particle size distribution in the support in fact makes it possible to obtain the desired variations in the mechanical and optical properties, without it being necessary to vary the nature of the resin as a function of the region of the support. The production of the composite block is thereby considerably simplified.

Preferably, the resin is chemically polymerizable, thermopolymerizable, or thermoplastic. In one preferred embodiment, the resin in the liquid state comprises substantially no particles.

In one embodiment, the resin in the liquid state comprises no pigment (particle of nanomtric size), or even no solid particle.

In order to facilitate the penetration of the resin in the liquid state, it is in fact preferable for it to have a low viscosity. In particular, it should not be of pasty nature. Where appropriate, the viscosity may be reduced by moderate heating.

The nature of the resin is not limiting.

The resin may in particular be chosen from the polymerizable resins described in U.S. Pat. Nos. 5,869,548, 5,843,348 and EP 0 701 808.

Preferably, the resin is chosen from the following list:
- a chemically polymerizable or thermopolymerizable monomer resin, preferably a vinyl ester or acrylic resin. The resin may in particular be chosen from the group made up of 2-hydroxyethyl methacrylate, CAS 868-77-9 (HEMA), tetraethylene glycol dimethacrylate, CAS 109-17-1 (TEGDMA), 2,2-bis(4-(2-hydroxy-3-methacryloyloxypropoxy)phenyl)propane, CAS 1565-94-2 (BIS-GMA), urethane dimethacrylate 1,6-bis (methacryloxy-2-ethoxycarbonylamino)-2,4,4-trimethyl-hexane, (UDMA) CAS 72869-86-4, ethylene glycol dimethacrylate (EGDMA), diethylene glycol dimethacrylate (DEGDMA), bisphenol A dimethacrylate, CAS 109-17-1 (BADMA);
- a thermoplastic resin, in particular chosen from saturated polyesters, and in particular polyethylene terephthalate (PET) and poly(1,4-butylene terephthalate), CAS 24968-12-5 (PBT), the poly(bisphenol A carbonate) polycarbonates, CAS 25037-45-0 (PC), bisphenol A carbonate, and polyamides.

In order to catalyze the chemically polymerizable impregnation materials, it is possible to use peroxides, and in particular dibenzoyl peroxide, CAS 94-36-0, methyl ethyl ketone peroxides, CAS 1338-23-4, di-tert-amyl peroxide, CAS 10508-09-5, di-tert-butyl peroxide, CAS 110-05-4, or cumene hydroperoxide, CAS 80-15-9.

In order to accelerate the curing with dibenzoyl peroxide, CAS 94-36-0, it is possible to use dimethylaniline (DMA), diethylaniline (DEA) or dimethyl-para-toluidine (DMPT). In order to accelerate the curing with methyl ethyl ketone peroxides, CAS 1338-23-4, it is possible to use, in particular, cobalt(II) 2-ethylhexanoate.

Preferably, a vacuum is created in the support before the beginning of the infiltration of the resin in the liquid state. This vacuum preferably corresponds to a pressure of less than 100 mbar, preferably less than 20 mbar. Advantageously, the vacuum promotes the penetration of the resin in the liquid state.

The term "$V_P(1)$" is used to refer to the total open pore volume of the porous support, before any infiltration of resin, measured at a temperature of 20° C. and under a pressure of 1 bar (ambient pressure).

The term "$V_L(1)$" is used to refer to the volume of resin in the liquid state infiltrated into the support, measured at a temperature of 20° C. and under a pressure of 1 bar.

In a first embodiment, the resin in the liquid state fills the open pore volume $V_P(1)$ by capillary action, at low pressure, conventionally at ambient pressure. The volume of resin in the liquid state infiltrated into the support, $V_L(1)$, is thus substantially equal to the open pore volume $V_P(1)$.

The infiltration by the resin in the liquid state may be carried out at atmospheric pressure or under a pressure higher than atmospheric pressure. An infiltration at atmospheric pressure is advantageously simple to implement, but requires the use of a low-viscosity resin in the liquid state. An infiltration under a higher pressure is also possible, and may even be necessary if the resin in the liquid state has too high a viscosity.

However, on curing, the resin shrinks such that the volume occupied by the resin in the solid state $V_M(1)$ is less than the open pore volume $V_P(1)$. For example, the shrinkage resulting from a polymerization at ambient temperature may conventionally result in a decrease in the volume occupied by the resin of between 6% and 15% of its initial volume. This results in high tensile stresses at the interface between the resin and the surface of the support defining the pores, which may result in a detachment of the resin, and therefore in a reduction of the lifetime of the dental prosthesis, making it unfit for commercialization. Preferably, in a second preferred embodiment, the resin impregnating the support is cured in the liquid state, while the resin is subjected to a high pressure, greater than 300 bar.

Preferably, a volume of resin in the liquid state $V_L$ which is at least 2%, preferably at least 5%, preferably at least 10%, or even at least 15% greater than the volume $V_P$ of the open pores of the support is made to penetrate into and to cure in the support, the volumes $V_L$ and $V_P$ being measured at a temperature of 20° C. and under a pressure of 1 bar. In other words, to measure the volume $V_L$, the resin, in the liquid state, which has been infiltrated into the pores of the support under high pressure (the volume of which, at the time of this infiltration, corresponds substantially to the volume $V_P$ of open pores of the support) is taken into consideration, but while taking into consideration the volume occupied by this resin, in the liquid state, at a temperature of 20° C. and a pressure of 1 bar, that is to say before it is placed under pressure.

The infiltrated resin in the liquid state may in particular be subjected to a pressure greater than 400 bar, preferably greater than 500 bar, greater than 1000 bar, greater than 2000 bar, greater than 3000 bar, greater than 4000 bar, or even greater than 5000 bar. These high pressures increase the densities of the resin in the liquid state and the material constituting the support. However, the compressibility of the resin in the liquid state is greater than that of the material constituting the support. The amount of resin in the liquid state that it is possible to infiltrate, per unit of volume of the open pores, is therefore greater than the amount that it would be possible to infiltrate by applying only lower pressures, and in particular atmospheric pressure.

The placing under high pressure results in a reduction in the volume of the resin, thereby making it possible to obtain a volume of resin in the liquid state $V_L$ that is at least 2%, preferably at least 5%, preferably at least 10%, or even at least 1.5%, greater than the volume $V_P$ of the open pores of the support.

By making the resin in the liquid state cure under pressure, it thus becomes possible, after return to atmospheric pressure, to create prestresses compressing the resin. This results in a considerably improved mechanical strength.

The high pressure must be exerted on the resin infiltrated into the support while it is still in the liquid state and until it has at least partially cured. Preferably, all of the resin in the liquid state impregnating the support is cured before a return to atmospheric pressure. Preferably, the pressure is maintained substantially constant until all of the infiltrated resin has cured.

The high pressure may also be exerted during all or part of the infiltration phase, thereby advantageously facilitating the penetration of the resin in the liquid state, and thus permitting the use of more viscous resins.

Preferably, the high pressure is exerted isostatically, or "uniaxially". All the known pressurizing processes may be used.

Advantageously, in the second preferred embodiment, the composite block obtained then exhibits no mechanical stresses tending to detach the resin from the support (tensile stresses on the resin). On the contrary, the "overvolume" of the infiltrated and cured resin is preferably determined, as a function of the resin and of the support, so as to create a prestress, that is to say a permanent pressure between resin in the solid state and the support. In other words, the resin in the solid state is preferably compressed by the sintered support. The mechanical strength of the composite block is thereby considerably increased.

As an alternative to the placing under high pressure described above or, preferably in addition to this placing under high pressure, the infiltration of the resin in the liquid state is continued, where appropriate under pressure, during the curing of the already infiltrated resin and, likewise preferably, this curing is controlled in such a way that it is carried out from the interior of the support to its periphery. Advantageously, the cured resin does not therefore oppose the penetration of the additional resin in the liquid state within the support. It is thus possible to compensate for the decrease in the volume occupied by the infiltrated resin owing to the curing thereof, and beyond that, to compress the resin in the solid state.

In order to control the curing, it is in particular possible to act on one or more of the following parameters:
the concentration of accelerator and/or of catalyst in the resin in the liquid state;
the temperature and the period of time during which this temperature is maintained;
the chemical nature of the resin.

Preferably, the optimal conditions, and in particular the high pressure optionally used in step F) and optionally in step E) are determined, as a function of the resin and of the support, by measurements of the homogeneity of the microhardness, of the mechanical strength and of the optical properties.

The resin may in particular be a chemically polymerizable resin, conventionally mixed with a catalyst and with an accelerator, infiltrated for example with a pressure of 500 bar and at a temperature of between 80° C. and 1010° C.

The resin may also be a thermoplastic resin infiltrated for example under an isostatic pressure of 2500 bar, at 250° C., into a support previously placed under vacuum and heated to 250° C. The thermoplastic resin may also be infiltrated, for example, at a pressure of 3500 bar, at a temperature of 300° C., into a support previously placed under vacuum and heated to a temperature of 300° C.

For example, when the resin is chemically polymerizable, it is possible to add thereto a variable amount of accelerator. At the beginning of the infiltration, for example, it is possible to infiltrate a resin comprising a high amount of accelerator, and then, as the infiltration proceeds, to decrease the concentration of accelerator in the resin infiltrated.

The nature of the resin may also be variable. For example, it is possible, at the beginning of infiltration, to infiltrate a first thermopolymerizable resin at a first temperature, then to infiltrate a second thermopolymerizable resin at a second temperature higher than the first temperature. For example, the infiltration may begin with benzoyl peroxide, which is polymerizable at 80° C., then continue with di-t-butyl-1,2, 1-peroxide or di-t-amyl-1,4,2-peroxide or else comyl-1,8,8-peroxide, which are polymerizable at 120° C. To control the curing, it is then sufficient to heat the support to a temperature of between 80° C. and 120° C., for example 90° C., so as to cure only the first resin, at the core of the support, and then to heat this support to more than 120° C. in order to cure the second resin at the periphery. An infiltration under a pressure of approximately 2000 bar is advantageous. As a variant, it is possible to first infiltrate at the core of the support a chemically polymerizable resin, for example a first resin mixed with a catalyst and an accelerator, and then to infiltrate at its periphery a thermopolymerizable resin, for example a second resin mixed with a catalyst. The curing of the peripheral resin may then be carried out, by heating for example between 80° C. and 100° C., after curing of the resin placed at the core of the support. An infiltration under a pressure of approximately 1500 bar is advantageous. Where appropriate, the composite block is subjected to a heat treatment suitable for finishing the polymerization, for example of 100° C. for one hour.

Composite Block Produced from the Porous Support

The invention also relates to a composite block comprising a support according to the invention, impregnated with a resin in solid state 30 (FIG. 5), preferably produced according to a production process according to the invention, and in particular with curing, at least of a part of the resin, under high pressure (second preferred embodiment). Preferably, the support is conformed such that the composite block may be machined by a CAD-CAM device, in particular by a machining device such as the Celay® system from the company Mikrona or Cerec 3 from the company Sirona. Where appropriate, the composite block may integrate one or more members allowing the support to be held by such devices.

Figure 5:
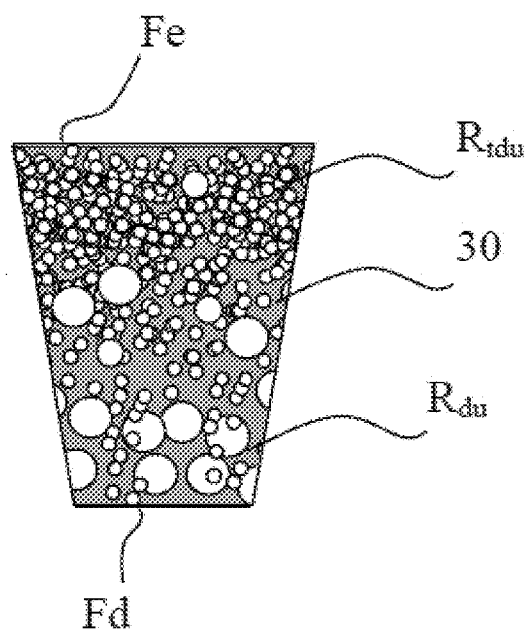
FIG. 5 represents very diagrammatically a composite block in one preferred embodiment of the invention.

As represented in FIG. 5, the composite block comprises:
a region having a hardness greater than 240 Vickers, termed "very hard region" $R_{tdu}$, and preferably a Young's elastic modulus, measured according to ISO standard 10 477, greater than 30 GPa, and
a region having a hardness greater than 60 Vickers and less than 180 Vickers, termed "hard region" $R_{du}$, and preferably a Young's elastic modulus, measured according to ISO standard 10 477, greater than 15 GPa and less than 30 GPa.

Preferably, each of said hard and very hard regions has a volume greater than 30 mm$^3$, preferably greater than 50 mm$^3$, preferably greater than 100 mm$^3$, preferably greater than 150 mm$^3$. Likewise preferably, said very hard and hard regions are in the form of layers of thickness greater than 1 mm, preferably greater than 3 mm, preferably greater than 5 mm Preferably, the very hard region $R_{tdu}$ has a hardness greater than 250 Vickers, preferably greater than 300 Vickers, preferably greater than 350 Vickers, or even greater than 400 Vickers, and/or preferably less than 450 Vickers.

Preferably, the hard region $R_{du}$ has a hardness greater than 70 Vickers, preferably greater than 80 Vickers, and/or less than 180 Vickers, preferably less than 170 Vickers, or even less than 160 Vickers, or less than 150 Vickers.

Preferably, the very hard region $R_{tdu}$ has a Young's elastic modulus, measured according to ISO standard 10 477, greater than 35 GPa, preferably greater than 40 GPa, and/or preferably less than 60 GPa.

Preferably, the hard region $R_{du}$ has a Young's elastic modulus, measured according to ISO standard 10 477, greater than 16 GPa, preferably greater than 18 GPa, and/or less than 28 GPa, preferably less than 25 GPa.

Advantageously, these mechanical properties confer a long lifetime on the dental prosthesis obtained from this composite block.

The very hard region may be included in a porous region or vice versa. Preferably, the very hard region is substantially amalgamated with a porous region.

The hard region may be included in a very porous region or vice versa. Preferably, the hard region is substantially amalgamated with a very porous region.

Process for Producing a Dental Prosthesis

The invention also relates to a process for producing a dental prosthesis, comprising an operation of machining a composite block according to the invention, and also a dental prosthesis produced or capable of having been produced according to a process in accordance with the invention.

A process for producing a composite dental prosthesis according to the invention may comprise the following steps:
1) preparing a porous support according to the invention;
2) optionally, rectifying the shape of the porous support;
3) optionally, carrying out a silanizing treatment at the surface of the open pores of the porous support;
4) impregnating the porous support with a resin in the liquid state;
5) curing the resin in the liquid state infiltrated into the porous support, optionally followed by a consolidating heat treatment;
6) final shaping.

The silanizing treatment, in step 3), is intended to increase the wettability of the surface of the pores by the resin in the liquid state, and in particular intended to make this surface more hydrophobic. Preferably, this silanizing treatment comprises a silanization by means of alkoxysilane, of halosilane, preferably of 3-methacryloxypropyltrimethoxysilane. After application of the silanizing agent, the support is dried, preferably at a temperature of between 100° C. and 200° C., conventionally for several hours.

The silanizing treatment may for example be carried out in accordance with the process described in U.S. Pat. No. 5,869,548.

Steps 4) and 5) correspond to steps E) and F) of a process for producing a composite block according to the invention, as described above.

EXAMPLES

The following example is provided for illustrative and non-limiting purposes.

The following powders were mixed:
30% by volume of a powder of alumina particles having percentiles $D_{10}$ of 0.5 µm, $D_{50}$ of 3 µm and $D_{90}$ of 6 µm, providing in particular enamel particles, and
70% by volume of a powder of alumina particles having percentiles $D_{10}$ of 2 µm, $D_{50}$ of 5.5 µm and $D_{90}$ of 8 µm, providing in particular dentine particles.

The group of particles thus formed was mixed with water, so as to constitute a suspension. The solids (alumina particles) represented 50% of the volume of the suspension.

0.05% of citric acid (binder), as a percentage of the mass of said suspension, were added. The group was mixed by means of a planetary mixer, then centrifuged so as to apply an acceleration of 150 G for 30 minutes. The mass centrifuged had the following dimensions:
1: 40 mm; w: 20 mm the 16 mm.

The supernatant was discarded.

The Ve/(Ve+Vd) ratio in proximity to the face of the centrifuged mass close to the axis of rotation (enamel face) was 0.9.

The region of the preform extending from the enamel face to a plane parallel to the enamel face and defined so that said region represents 25% of the volume of the support, constituted an "enamel region".

The Ve/(Ve+Vd) ratio in proximity to the opposite face (dentine face), distant from the axis of rotation, was 0.1.

The region of the preform extending from the dentine face to a plane parallel to the dentine face and defined so that said region represents 25% of the volume of the support, constituted a "dentine region".

The mass centrifuged was then dried at 20° C. for 24 hours, which resulted in a preform.

The preform was removed from the mold, then introduced into a furnace, the enamel face being placed on a hot plate placed beforehand in the furnace.

The furnace was brought to 1100° C. for 4 hours, in order to ensure substantially homogeneous basic sintering of the preform.

The hot plate on which the enamel face is placed was then turned on, while maintaining the furnace at 1100° C., such that the enamel face is brought to a temperature of 1300° C. for 1.5 hours, and thus undergoes additional sintering.

The heat treatment resulted in a porous support having a mean open porosity of 40%.

The region of porous support extending from the enamel face to a plane parallel to the enamel face and defined so that said region represents 25% of the volume of the support, had a mean pore size, measured with a mercury porosimeter, of 0.2 µm. It constituted a "porous region".

The region of the porous support extending from the dentine face to a plane parallel to the dentine face and defined so that said region represents 25% of the volume of the support, had a mean pore size of 0.3 µm. It constituted a "very porous region".

The porous support underwent successively:
a silanizing treatment with a solution having the following composition, as weight percents:
methoxypropanol: 93.8%
water: 5%
acetic acid: 0.2%
silane: 1%
drying at 150° C. for 4 hours;
placing under vacuum;
infiltration of a resin at a temperature of 60° C. under a pressure of 80 bar, for 4 hours, the weight composition of this resin being the following:
UDMA 99%
DI-TERT-AMYL PEROXIDE: 1%
heating at 150° C. under a pressure of 2000 bar, for 1 hour in order to polymerize the resin.

In practice, it is possible, after the silanizing operation, to place the porous support in a latex mold, to apply a vacuum thereto, for example up to a pressure of approximately 100 mbar, and then to introduce therein the resin in the liquid state under vacuum and to close the mold. After infiltration, the mold thus closed may then be introduced into a pot or into an autoclave where it is gradually subjected to the pressure of 2000 bar and to the resin consolidation heating, before cooling and a return to atmospheric pressure.

The porous region of the support corresponded to a "very d region" having a hardness of 380 Vickers and a Young's elastic modulus of 55 GPa.

The very porous region of the support corresponded to a "hard region" having a hardness of 160 Vickers and a Young's elastic modulus of 25 GPa.

As is presently clearly apparent, the invention makes it possible to obtain a continuous and gradual variation in the optical and/or mechanical properties of a composite block intended for the production of a dental prosthesis. It thus makes it possible to produce a dental prosthesis, the appearance and the mechanical properties of which are substantially identical to those of a natural tooth.

Of course, the invention is not limited to the embodiments described, nor to the examples. In particular, the infiltration of the resin in the liquid state may be limited to a limited region of the support, and in particular may be limited to its peripheral region.

The invention claimed is:

1. A preform intended for the production of a dental prosthesis, said preform comprising a group of agglomerated ceramic, glass-ceramic or glass particles, such that, as volume percents:
   more than 40% and less than 90% of the agglomerated ceramic, glass-ceramic or glass particles of said group have a size greater than 0.5 µm and less than 3.5 µm, said agglomerated ceramic, glass-ceramic or glass particles hereinafter being denoted "enamel particles", and
   more than 10% and less than 60% of the agglomerated ceramic, glass-ceramic or glass particles of said group have a size greater than 3.5 µm and less than 5.5 µm, said agglomerated ceramic, glass-ceramic or glass particles hereinafter being denoted "dentine particles",
   a microstructure of the preform, obtainable by a centrifugation of a suspension containing said particles, being such that there is an axis X, termed "axis of variation," along which the Ve/(Ve+Vd) ratio changes continuously, Ve and Vd denoting the volume percents of enamel particles and of dentine particles, respectively,
   wherein, along the axis of variation X, the fewer dentine particles a region of said preform comprises, the more enamel particles said region comprises,
   the enamel and dentine particles representing, together, more than 90% of the volume of the agglomerated ceramic, glass-ceramic or glass particles,
   the agglomerated ceramic, glass-ceramic or glass particle size distribution of said group of particles being bimodal and comprising first and second principle modes, the first principle mode being greater than 1.5 µm and less than 3.5 µm, the second mode being greater than 3.5 µm and less than 5.5 µm.

2. The preform as claimed in claim 1, wherein the enamel particles have a mean size $D_{50}$ greater than 1.5 µm and less than 3.0 µm, and/or the dentine particles have a mean size $D_{50}$ greater than 4.0 µm and less than 5.0 µm.

3. The preform as claimed in claim 1, wherein, as volume percents, more than 50% of the agglomerated ceramic, glass-ceramic or glass particles of said group are enamel particles, and/or more than 30% of the agglomerated ceramic, glass-ceramic or glass particles of said group are dentine particles.

4. The preform as claimed in claim 1, in which, along the axis of variation, the volume percent of enamel particles varies inversely opposite to the volume percent of dentine particles.

5. The preform as claimed in claim 1, wherein the preform has a first region, termed "enamel region", in which the Ve/(Ve+Vd) ratio is greater than 0.9 and a second region, termed "dentine region", in which the Ve/(Ve+Vd) ratio is less than 0.1,
the enamel and dentine regions being in the form of layers and extending from opposite enamel (Fe) and dentine (Fd) faces of the preform, taking into consideration the axis of variation.

6. The preform as claimed in claim 5, said dentine region having a Ve/(Ve+Vd) ratio of less than 0.05.

7. The preform as claimed in claim 1, wherein the enamel and dentine particles represent, together, more than 80% of the volume of the mass of said group of agglomerated ceramic, glass-ceramic or glass particles.

8. The preform as chimed in claim 7, wherein the enamel and dentine particles represent, together, more than 90% of the volume of the mass of said group of agglomerated ceramic, glass-ceramic or glass particles.

9. The preform as claimed in claim 1, wherein more than 90% by volume of agglomerated ceramic, glass-ceramic or glass particles are made of one and the same material.

10. A preform intended for the production of a dental prosthesis, said preform comprising a group of agglomerated ceramic, glass-ceramic or glass particles, such that, as volume percents:
    more than 40% and less than 90% of the agglomerated ceramic, glass-ceramic or glass particles of said group have a size greater than 0.5 µm and less than 3.5 µm, said agglomerated ceramic, glass-ceramic or glass particles hereinafter being denoted "enamel particles", and
    more than 10% and less than 60% of the agglomerated ceramic, glass-ceramic or glass particles of said group have a size greater than 3.5 µm and less than 5.5 µm, said agglomerated ceramic, glass-ceramic or glass particles hereinafter being denoted "dentine particles",
    a microstructure of the preform being such that there is an axis X, termed "axis of variation," along which the Ve/(Ve+Vd) ratio changes continuously, Ve and Vd denoting the volume percents of enamel particles and of dentine particles, respectively,
    the enamel and dentine particles representing, together, more than 90% of the volume of the agglomerated ceramic, glass-ceramic or glass particles,
    the agglomerated ceramic, glass-ceramic or glass particle size distribution of said group of particles being bimodal and comprising first and second principle modes,
    the first principle mode being greater than 1.5 µm and less than 3.5 µm, the second mode being greater than 3.5 µm and less than 5.5 µm,
    wherein the preform has a first region, termed "enamel region", in which the Ve/(Ve+Vd) ratio is greater than 0.9 and a second region, termed "dentine region", in which the Ve/(Ve+Vd) ratio is less than 0.1,
    the enamel and dentine regions being in the form of layers and extending from opposite enamel (Fe) and dentine (Fd) faces of the preform, taking into consideration the axis of variation.

11. The preform as claimed in claim 10, said dentine region having a Ve/(Ve+Vd) ratio of less than 0.05.

* * * * *